United States Patent
Amano et al.

(10) Patent No.: US 8,570,148 B2
(45) Date of Patent: Oct. 29, 2013

(54) BIOLOGICAL INFORMATION ACQUIRING APPARATUS, BIOLOGICAL INFORMATION ACQUIRING METHOD AND BIOMETRIC AUTHENTICATION APPARATUS

(75) Inventors: Kazuhiko Amano, Suwa (JP); Koichi Shimizu, Sapporo (JP)

(73) Assignees: Seiko Epson Corporation, Tokyo (JP); National University Corporation Hokkaido University, Sapporo-shi (JP)

( * ) Notice: Subject to any disclaimer, the term of this patent is extended or adjusted under 35 U.S.C. 154(b) by 829 days.

(21) Appl. No.: 12/721,078

(22) Filed: Mar. 10, 2010

(65) Prior Publication Data
US 2010/0237990 A1      Sep. 23, 2010

(30) Foreign Application Priority Data
Mar. 12, 2009   (JP) .................. 2009-060043

(51) Int. Cl.
    *G05B 19/00*   (2006.01)
(52) U.S. Cl.
    USPC .......................... 340/5.82; 382/115
(58) Field of Classification Search
    USPC ............... 600/300; 382/115; 340/5.82
    See application file for complete search history.

(56) References Cited

U.S. PATENT DOCUMENTS

2007/0253602 A1*   11/2007   Amano .................. 382/115
2007/0270666 A1*   11/2007   Amano et al. ............. 600/300

FOREIGN PATENT DOCUMENTS

JP      A 2007-330769       12/2007

* cited by examiner

*Primary Examiner* — Steven Lim
*Assistant Examiner* — Kaleria Knox
(74) *Attorney, Agent, or Firm* — Oliff and Berridge, PLC

(57) ABSTRACT

A biological information acquiring apparatus includes light source units configured to irradiate light onto a living body, a light receiving unit including a light receiving element, the light receiving element including pixels, each of the pixels receiving at least one of a transmission light and a reflection light, and a nonuniform filter disposed on the light receiving unit and on a light path of at least one of the transmission light and the reflection light, the nonuniform filter having a light transmittance that varies with area of the nonuniform filter. The light source units are disposed around the light receiving unit discretely, and the light transmittance of the nonuniform filter is set so that a light intensity of at least one of the transmission light and the reflection light is uniform over an entire surface of the light receiving element.

6 Claims, 5 Drawing Sheets

BIOLOGICAL INFORMATION ACQUIRING APPARATUS, BIOLOGICAL INFORMATION ACQUIRING METHOD AND BIOMETRIC AUTHENTICATION APPARATUS

BACKGROUND

1. Technical Field

The present invention relates to a biological information acquiring apparatus, a biological information acquiring method and a biometric authentication apparatus.

Priority is claimed on Japanese Patent Application No. 2009-060043, filed Mar. 12, 2009, the content of which is incorporated herein by reference.

2. Related Art

A biometric authentication has been performed that uses biological information such as a fingerprint, an iris, or a vein pattern of a user to identify the user as a qualified user. Various kinds of biological information acquiring apparatuses are used to perform such biometric authentication.

Some of these biological information acquiring apparatuses include a light source unit that emits a light and a light receiving element that receives the light. The biological information is obtained by irradiating the light from the light source unit to a living body, receiving the light from the body, and converting the light that is received to an electrical signal.

Devices such as a mobile terminal and a personal computer that have an authentication function are used today. A biological information acquiring apparatus that is large in scale and requires high power consumption is undesirable.

The authentication is required to have higher accuracy than before, as public awareness of security has been increased. Therefore, it is required to increase the accuracy of the biological information that is obtained. Japanese Unexamined Patent Application, First Publication No. 2007-330769 discloses a biometric authentication apparatus that obtains biological information with high accuracy and can be miniaturized easily.

The biometric authentication apparatus of Japanese Unexamined Patent Application, First Publication No. 2007-330769 includes a light source unit that is disposed around a light receiving unit of the biometric authentication apparatus. The light source unit is in a circular form, and a unit that concentrates the received light is necessary. Accordingly, it is difficult to miniaturize the biometric authentication apparatus.

SUMMARY

The invention provides a biological information acquiring apparatus that can be miniaturized, a biological information acquiring method, and a biometric authentication apparatus.

A biological information acquiring apparatus may acquire biological information of a living body by irradiating a light onto the body. The biological information acquiring apparatus may include light source units configured to irradiate light onto the body, a light receiving unit including a light receiving element, the light receiving element including pixels, each of the pixels receiving at least one of a transmission light and a reflection light by irradiating the light from the light source units onto the body, the transmission light transmitting through the body, the reflection light reflected by the body, and a nonuniform filter disposed on the light receiving unit and on a light path of at least one of the transmission light and the reflection light, the nonuniform filter having a light transmittance that varies with area of the nonuniform filter. The light source units may be disposed around the light receiving unit discretely, and the light transmittance of the nonuniform filter is set so that a light intensity of at least one of the transmission light and the reflection light is uniform over an entire surface of the light receiving element.

The biological information acquiring apparatus can make the light intensity of the light, which is received by the light receiving element that has a plurality of pixels, uniform over the entire surface of the light receiving element. Accordingly, the light intensity can be uniform over the entire surface of the light receiving element having the plurality of pixels, which is independent of the distance from the light source units. Therefore, even if the dynamic range of the received light is small, and the quality of the acquired biological information can be improved. The light source units are disposed discretely and the biological information acquiring apparatus can be made small easily.

The nonuniform filter may include a distant part that is distant from the light source units and a near part that is near the light source units, the light transmittance of the distant part is set high, and the light transmittance of the near part is set low.

The biological information acquiring apparatus can make the light intensity, which is transmitted through the nonuniform filter, uniform over the entire output surface of the nonuniform filter. The light intensity can be uniform over the entire surface of the light receiving element having the plurality of pixels, which is independent of the distance from the light source units.

The biological information acquiring apparatus may be attachable to a body.

The biological information acquiring apparatus can use the biological information in various situations and its usability can be increased.

Each of the light source units may include an LED. The number of the light source units may be determined based on the calculation of a difference of the light intensity between a first area of the light receiving unit and a second area of the light receiving unit and a threshold value of the difference of the light intensity. The light intensity in the first area is smallest in the light receiving unit, and the light intensity in the second area is largest in the light receiving unit. The light intensity is calculated based on a temporarily defined number of light source units, an area of the light receiving unit, coordinates of the LED when a center of the light receiving unit is defined as an origin, an equivalent scattering coefficient of the body, an absorption coefficient of the body, and a formula for computation of a light intensity distribution of a diffusely reflected light.

Accordingly, the number of the light source units included in the biological information acquiring apparatus can be optimal.

A biological information acquiring method may acquire biological information of a living body by irradiating a light onto the body. The biological information acquiring method may include irradiating the light that is irradiated from each of light source units onto the body, the light source units being disposed around a light receiving unit discretely and receiving at least one of transmission light transmitting through the body and reflection light reflected by the body by irradiating the light from the light source units onto the body, the receiving being performed by a light receiving element including pixels through a nonuniform filter that is disposed on a light path of at least one of the transmission light and the reflection light, the nonuniform filter having a light transmittance that varies with area of the nonuniform filter. The light transmittance of the nonuniform filter may be set so that a light intensity of at least one of the transmission light and the reflection light is uniform over an entire surface of the light receiving element.

The biological information acquiring apparatus can make the light intensity of the light, which is received by the light receiving element that has a plurality of pixels, uniform over the entire surface of the light receiving element. Accordingly, the light intensity can be uniform over the entire surface of the light receiving element having the plurality of pixels, which is independent of the distance from the light source units. Therefore, the dynamic range of the received light is small, and the quality of the acquired biological information can be improved. The light source units are disposed discretely and the biological information acquiring apparatus can be made small easily.

The number of the light source units may be determined based on the calculation of a difference of the light intensity between a first area of the light receiving unit and a second area of the light receiving unit and a threshold value of the difference of the light intensity. The light intensity in the first area is smallest in the light receiving unit, and the light intensity in the second area is largest in the light receiving unit. The light intensity is calculated based on a temporarily defined number of light source units, an area of the light receiving unit, coordinates of each LED included in the light source units when a center of the light receiving unit is defined as an origin, a reduced scattering coefficient of the living body, an absorption coefficient of the body, and a formula for computation of a light intensity distribution of a diffusely reflected light.

Accordingly, the number of the light source units included in the biological information acquiring apparatus can be optimal.

A biometric authentication apparatus may include a biological information acquiring apparatus configured to acquire biological information of a living body by irradiating a light onto the body, and an authentication unit configured to perform an authentication of a person based on the biological information of the body acquired by the biological information acquiring apparatus. The biological information acquiring apparatus may include light source units configured to irradiate the light onto the body, a light receiving unit including a light receiving element, the light receiving element including pixels, each of the pixels receiving at least one of a transmission light and a reflection light by irradiating the light from the light source units onto the body, the transmission light transmitting through the body, the reflection light reflected by the body, and a nonuniform filter disposed on the light receiving unit and on a light path of at least one of the transmission light and the reflection light, the nonuniform filter having a light transmittance that varies with area of the nonuniform filter. The authentication unit may include a biological information storing unit configured to store the biological information of the body acquired by the biological information acquiring apparatus as first information, and an authentication control unit configured to compare the first information and second information, the second information being the biological information of the body acquired by the biological information acquiring apparatus when the authentication is performed, the authentication control unit determining completion of the authentication and outputting an enable signal if the first information coincides with the second information. The light source units may be disposed around the light receiving unit discretely and the light transmittance of the nonuniform filter is set so that a light intensity of at least one of the transmission light and the reflection light is uniform over an entire surface of the light receiving element.

The biological information acquiring apparatus can make the light intensity of the light, which is received by the light receiving element that has a plurality of pixels, uniform over the entire surface of the light receiving element. Accordingly, the light intensity can be uniform over the entire surface of the light receiving element having the plurality of pixels, which is independent of the distance from the light source units. Therefore, the dynamic range of the received light is small, and the quality of the acquired biological information can be improved. The light source units are disposed discretely and the biological information acquiring apparatus can be made small easily.

Each of the light source units may include an LED. The number of the light source units may be determined based on the calculation of a difference of the light intensity between a first area of the light receiving unit and a second area of the light receiving unit and a threshold value of the difference of the light intensity. The light intensity in the first area is smallest in the light receiving unit, and the light intensity in the second area is largest in the light receiving unit. The light intensity is calculated based on a temporarily defined number of light source units, an area of the light receiving unit, coordinates of the LED when a center of the light receiving unit is defined as an origin, a reduced scattering coefficient of the living body, an absorption coefficient of the body, and a formula for computation of a light intensity distribution of a diffusely reflected light.

Accordingly, the number of the light source units included in the biological information acquiring apparatus can be optimal.

The biometric authentication apparatus may be attachable to a body.

The biometric authentication apparatus can use the biological information in various situations and its usability can be increased.

BRIEF DESCRIPTION OF THE DRAWINGS

The invention will be described with reference to the accompanying drawings, wherein like numbers reference like elements.

DESCRIPTION OF EXEMPLARY EMBODIMENTS

The invention will be now described herein with reference to illustrative embodiments. Those skilled in the art will recognize that many alternative embodiments can be accomplished using the teaching of the invention and that the invention is not limited to the embodiments illustrated for explanatory purpose.

Figure 1:
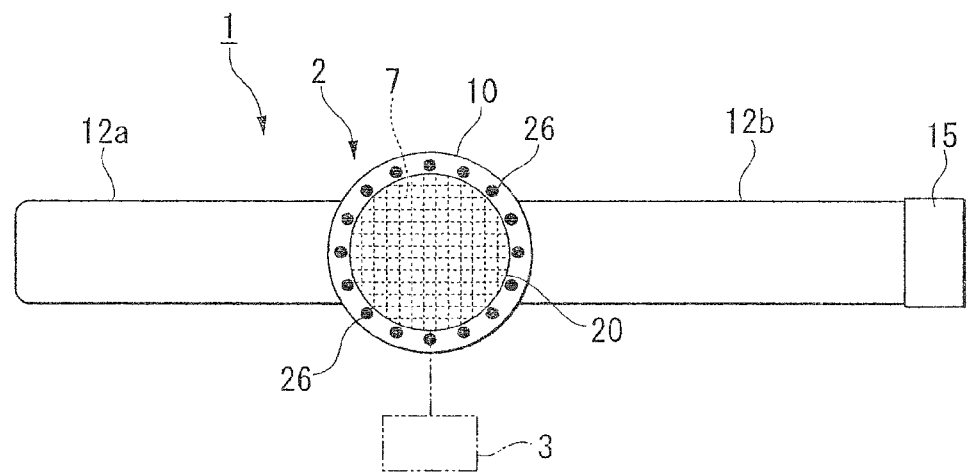
FIG. 1 is a diagram illustrating a plain view of a biometric authentication apparatus in accordance with a first embodiment of the invention.

A biometric authentication apparatus in accordance with a first embodiment of the invention will be described using the appended figures. FIG. 1 is a diagram illustrating a plain view of the biometric authentication apparatus 1 in accordance with the first embodiment of the invention.

The biometric authentication apparatus 1 includes a circular base unit 10 that is in a circular discform. The circular base unit 10 includes a band part 12a and a band part 12b that are on the same line and stretch toward the opposite sides of each other. A locking part 15 is in an end of the band part 12b. The locking part 15 of the band part 12b locks the end of the band part 12a.

Figure 2:
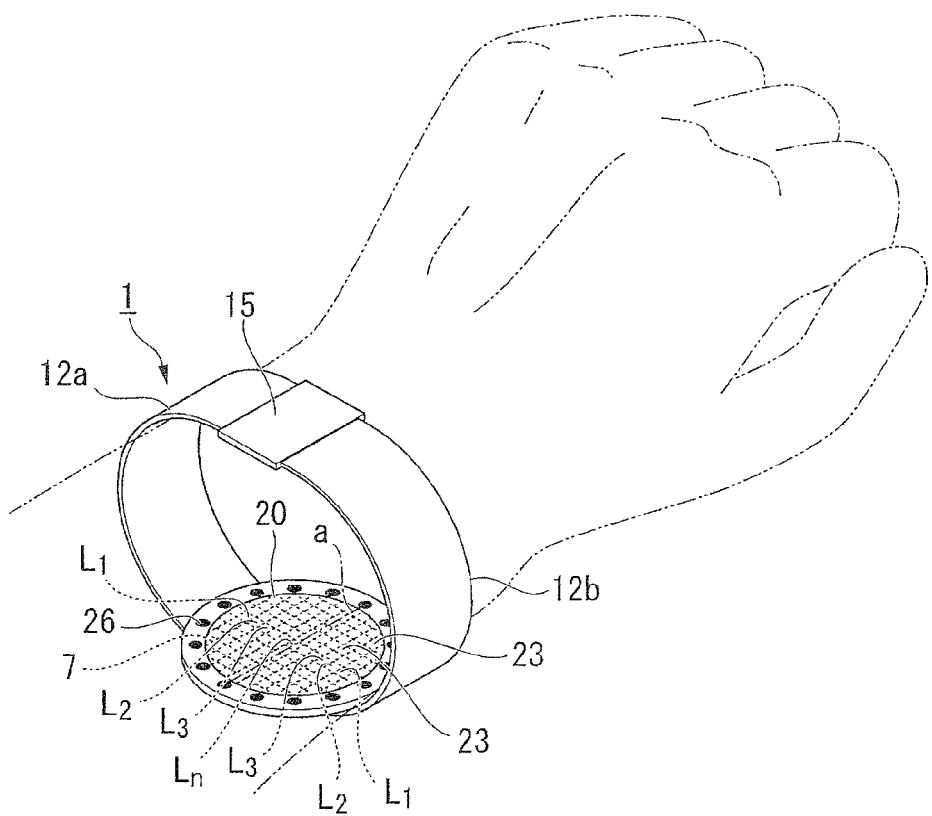
FIG. 2 is a diagram illustrating the biometric authentication apparatus of FIG. 1 that is worn around a person's wrist.

FIG. 2 is a diagram illustrating the biometric authentication apparatus 1 that is worn around a person's wrist. As illustrated in FIG. 2, the biometric authentication apparatus 1 is worn around the wrist by rolling the band part 12a and the band part 12b around the wrist and locking the locking part 15 to the end of the band part 12a.

As illustrated in FIG. 1, the biometric authentication apparatus 1 includes a biological information acquiring unit (biological information acquiring apparatus) 2 that obtains vein patterns of a living body and an authentication unit 3 that performs an authentication of a person using the vein patterns obtained by the biological information acquiring unit 2.

The biological information acquiring unit 2 includes a light receiving unit 7 that receives a light and a circular discrete light source unit (light source unit) 26 that is formed circularly and discretely and disposed around the light receiving unit 7. The circular discrete light source unit 26 consists of LEDs (Light-Emitting Diodes), for example. The light receiving unit 7 consists of CCDs (Charge Coupled Devices), for example. The light receiving unit 7 and the circular discrete light source unit 26 are disposed on a main surface that is one surface of the circular base unit 10.

Figure 3:
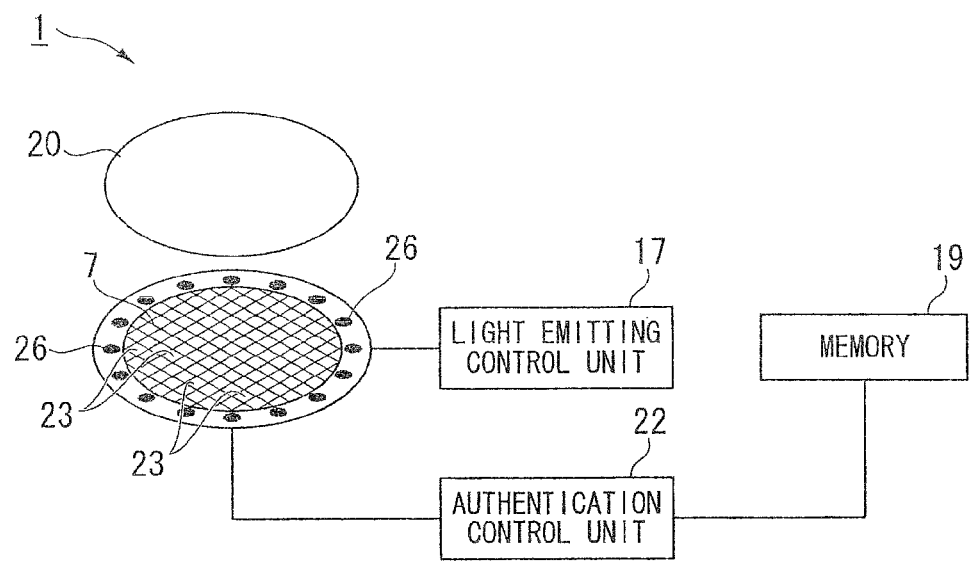
FIG. 3 is a block diagram illustrating functions of the biometric authentication apparatus of FIG. 1.

FIG. 3 is a block diagram illustrating functions of the biometric authentication apparatus of FIG. 1. As illustrated in FIG. 3, each LED of the circular discrete light source unit 26 is electrically connected to a light emitting control unit 17 that is included in the biometric authentication apparatus 1. Each LED of the circular discrete light source unit 26 emits a CW (Continuous Wave) light, which is controlled by the light emitting control unit 17.

The light receiving unit 7 includes light receiving elements 23, each of which is in a planar form and has pixels disposed in an array, and a micro lens array, which is disposed above each of the light receiving elements 23 and is not illustrated in the figure. When the biometric authentication apparatus 1 is worn around the wrist as illustrated in FIG. 2, the light receiving element that is disposed nearest to the circular discrete light source unit 26 is a light receiving element L1. From the nearest point to the circular discrete light source unit 26 to the farthest point from the circular discrete light source unit 26, the light receiving element L1, a light receiving element L2, a light receiving element L3, ..., a light receiving element Ln are disposed. The light receiving element Ln is disposed farthest from the circular discrete light source unit 26. That is, the light receiving element L1 is disposed at an outer edge part of the light receiving unit 7, and the light receiving element Ln is disposed at a center part of the light receiving unit 7.

As illustrated in FIG. 3, the light receiving unit 7 is electrically connected to an authentication control unit 22 that is included in the biometric authentication apparatus 1. The authentication control unit 22 performs the authentication of a person. The authentication control unit 22 is electrically connected to a memory unit (biological information storing unit) 19 that is included in the biometric authentication apparatus 1. The memory unit 19 stores vein pattern data that is an electrical signal from the light receiving unit 7. The authentication control unit 22 compares the vein pattern data, which is the electrical signal from the light receiving unit 7, to the vein pattern data, which has been stored beforehand in the memory unit 19. If the vein pattern data, which is the electrical signal from the light receiving unit 7, coincides with the vein pattern data, which has been stored beforehand in the memory unit 19, then it is determined that the authentication has completed and the authentication control unit 22 outputs an enable signal that enables use of external devices.

In the first embodiment, a nonuniform filter 20 that is in a circular form is disposed above the light receiving unit 7 on the main surface that is one surface of the circular base unit 10. If the biometric authentication apparatus 1 is worn around the wrist as illustrated in FIG. 2, then the nonuniform filter 20 is disposed on a light path of a reflected light from the wrist. The reflected light is made when, the CW light from the circular discrete light source unit 26 is reflected in the wrist. The reflected light is transmitted through the nonuniform filter 20 and received by the light receiving unit 7.

The light transmittance of the nonuniform filter 20 is set so that the light intensity distribution of the lights, which is received by the pixels included in the light receiving element 23, becomes uniform over the entire surface of the light receiving element 23. That is, the light transmittance of the nonuniform filter 20 is set so that the light intensities of the lights, which are transmitted through the nonuniform filter 20, become uniform over the entire surface of the nonuniform filter 20.

Figure 4:
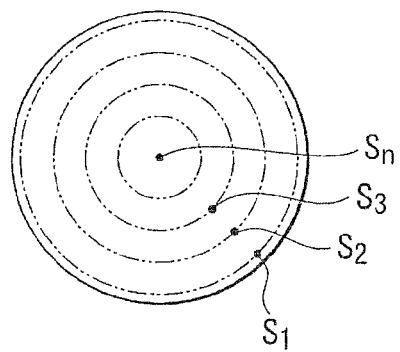
FIG. 4 is a diagram illustrating a nonuniform filter in the biometric authentication apparatus of FIG. 1.

FIG. 4 is a diagram illustrating the nonuniform filter 20 in the biometric authentication apparatus 1. The nonuniform filter 20 includes circumferences S1, S2, ..., Sn. The circumference S1 is disposed on the most outer edge of the nonuniform filter 20. The circumference Sn is disposed on the center of the nonuniform filter 20. The light transmittance of the circumference S1 is set to be the smallest of the light transmittances of the circumferences S1, ..., Sn. The light transmittance becomes larger as the circumference moves to the center of the nonuniform filter 20. The light transmittance of the circumference Sn on the center of the nonuniform filter 20 is set to be the largest of the light transmittances of the circumferences S1, ..., Sn.

If the biometric authentication apparatus 1 is worn around the wrist, then the circumference S1 is disposed in the nearest position to the circular discrete light source unit 26. As the circumference (S1, S2, S3, ..., Sn) goes to the center of the nonuniform filter 20, the distance between the circumference and the circular discrete light source unit 26 becomes lager. The center area of the circumference Sn is the farthest area from the circular discrete light source unit 26. If the biometric authentication apparatus 1 is worn around the wrist, then the light transmittance of the nonuniform filter 20 is the lowest in the nearest position to the circular discrete light source unit 26. The farther the position is from the circular discrete light source unit 26, the higher the light transmittance of the nonuniform filter 20 becomes. The light transmittance of the nonuniform filter 20 is set to be the highest in the farthest position from the circular discrete light source unit 26.

Behavior of the biometric authentication apparatus 1 in accordance with the first embodiment will be described.

First, the vein patterns of the qualified user are registered by the qualified user of the external device. As illustrated in FIG. 2, the biometric authentication apparatus 1 is worn around the wrist. The light receiving unit 7 is disposed facing toward the wrist. The light emitting control unit 17 outputs a driving signal to the circular discrete light source unit 26. If the circular discrete light source unit 26 receives the driving signal, then the circular discrete light source unit 26 emits the CW light. The CW light is reflected in the wrist to be the reflected light. The reflected light is transmitted through the nonuniform filter 20 and received by the light receiving unit 7.

The way of increasing the accuracy of the acquired biological information will be described.

The reflected light that is output from the circular discrete light source unit 26 and reflected in the wrist is transmitted to the nonuniform filter 20. The light intensity is the highest in the circumference S1, which is the nearest position to the circular discrete light source unit 26. The farther the position is from the circular discrete light source unit 26, the lower the light intensity becomes. The light intensity is the lowest in the farthest position from the circular discrete light source unit 26.

Figure 5:
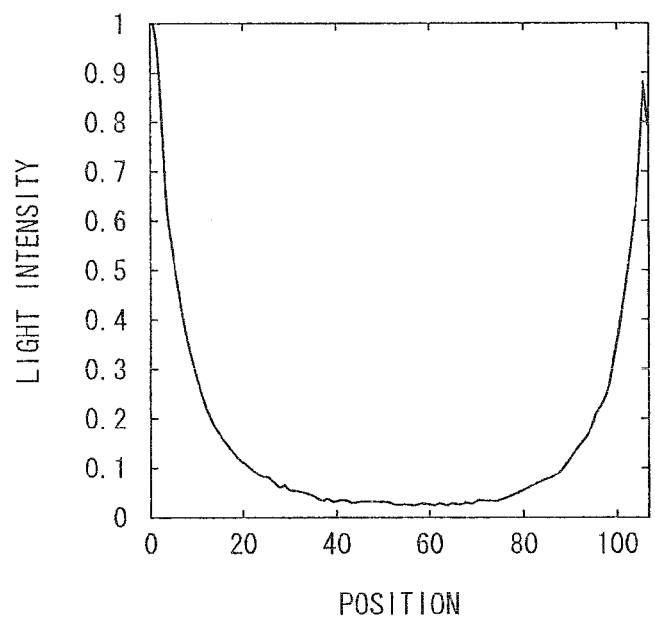
FIG. 5 is a graph showing a light intensity distribution on a line a of FIG. 2 when a uniform filter is used instead of the nonuniform filter of FIG. 1.

FIG. 5 is a graph showing the light intensity distribution when a uniform filter is used instead of the nonuniform filter 20.

As illustrated in FIG. 5, the light intensity in the outer edge of the filter is the highest. The light intensity becomes lower as moving to the center of the filter.

The light transmittance of the nonuniform filter 20 is set so that the light intensity distribution is uniform over the surface of the nonuniform filter 20. For example, the light transmittance of the nonuniform filter 20 in accordance with the first embodiment is set to be an inverse function of the light intensity of the uniform filter as illustrated in FIG. 5. The light transmittance of the nonuniform filter 20 is the lowest in the nearest position to the circular discrete light source unit 26. The farther the position is from the circular discrete light source unit 26, the higher the light transmittance becomes. The light transmittance is set to be the highest in the farthest position from the circular discrete light source unit 26.

The reflected light transmitted to the circumference S1 of the nonuniform filter 20 is mostly cut off at the circumference S1 and transmitted through the nonuniform filter 20. The light that is cut off becomes less as moving to the circumferences S2, S3, . . . , Sn. The light that is cut off at the circumference Sn near the center of the nonuniform filter 20 is the least. By this way, the light intensity of the reflected light that is transmitted through the nonuniform filter 20 becomes uniform over the entire surface of the nonuniform filter 20, and the light intensity distribution becomes uniform over the entire surface of the nonuniform filter 20.

Figure 6:
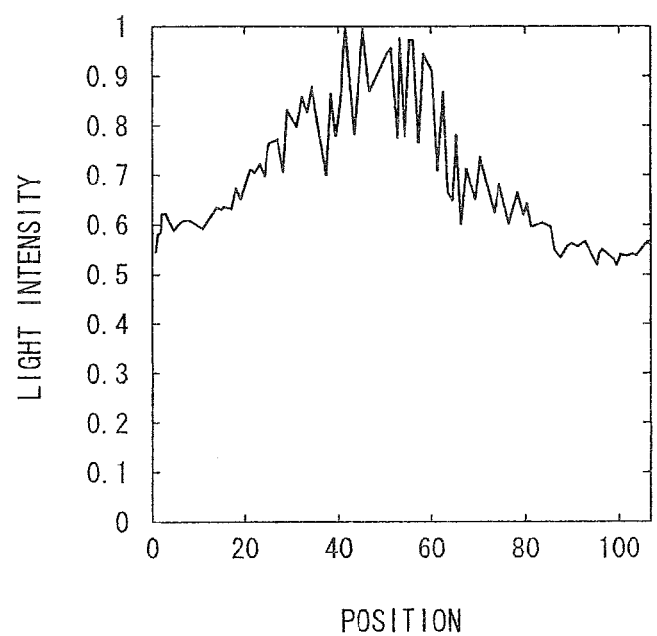
FIG. 6 is a graph showing the light intensity distribution on the line a of FIG. 2 when the nonuniform filter of FIG. 1 is used.

FIG. 6 is a graph showing the light intensity distribution when the nonuniform filter 20 is used. The fluctuation of intensity corresponds to the image signal from the vein.

As illustrated in FIG. 6, the difference between the light intensity at the outer edge of the nonuniform filter 20 and the light intensity at the center of the nonuniform filter 20 is remarkably decreased compared with the case of FIG. 5 that uses the uniform filter. The light intensity distribution is uniform over the entire surface of the nonuniform filter 20.

By this way, the dynamic range of the received light become small, and quality of the acquired biological information can be increased.

The reflected light with the uniform intensity over the entire surface of the nonuniform filter 20 is received by the light receiving unit 7. The light intensities of the lights that are received by the light receiving elements L1, L2, . . . , Ln become close each other. The electrical signal that is output from the light receiving unit 7 is stored in the memory unit 19 as the vein pattern data. By this way, the vein pattern data of the qualified user is registered.

Next, the way of the authentication will be described.

When the authentication is performed, the biometric authentication apparatus 1 is worn around the wrist and the vein patterns are acquired as described above. The authentication control unit 22 compares the vein pattern data that is the electrical signal output from the light receiving unit 7 and the vein pattern data stored in the memory unit 19 beforehand. If the authentication control unit 22 determines that the vein pattern data that is the electrical signal output from the light receiving unit 7 is equal to the vein pattern data stored in the memory unit 19 beforehand, then the authentication of the qualified user is regarded as a success and the authentication control unit 22 outputs the enable signal that enables the usage of the external device. If the authentication control unit 22 determines the vein pattern data that is the electrical signal output from the light receiving unit 7 is not equal to the vein pattern data stored in the memory unit 19 beforehand, then the authentication of the qualified user is regarded as a failure and the authentication control unit 22 outputs an inhibiting signal.

The biological information acquiring apparatus 1 in accordance with the first embodiment can make the light intensity of the light, which has been received by the light receiving element 23 that is in a planar form and has a plurality of pixels, uniform over the entire surface of the light receiving element 23. Accordingly, the light intensity can be uniform over the entire surface of the light receiving element 23 having the plurality of pixels, which is independent of a distance from the circular discrete light source unit 26. Therefore, the dynamic range of the received light become small, and the quality of the acquired biological information can be increased. As a result, the accuracy of the authentication can be improved.

The biological information acquiring apparatus 1 in accordance with the first embodiment is attachable to the wrist. Therefore, the biometric authentication can be performed in various situations and its usability can be increased.

The biological information acquiring apparatus 1 receives the reflected light that is reflected from the living body. Therefore, the position of the circular discrete light source unit 26 and the light receiving unit 7 can be fixed, and the vein patterns can be acquired quickly and accurately.

The light source units are disposed discretely, and the biological information acquiring apparatus 1 can be made small easily.

Next, the number of the LEDs included in the circular discrete light source unit 26 of the biometric authentication apparatus 1 in accordance with the first embodiment will be described.

The larger the number of the LEDs included in the circular discrete light source unit 26 is, the larger the biometric authentication apparatus 1 becomes. Therefore, it is preferable that the number of LEDs included in the circular discrete light source unit 26 is small. If the number of the LEDs included in the circular discrete light source unit 26 is small, then the intensity and the uniformity of the light that enters the living body is insufficient for authentication. Therefore, it is necessary that the number of the LEDs included in the circular discrete light source unit 26 is larger than a certain number.

The number of the LEDs is determined based on the light intensity distribution of diffusively reflected light when the light from the LED of the circular discrete light source unit 26 enters the living body (scattering substance) vertically. The light intensity distribution R(ρ) of the diffusively reflected light is calculated by the equation (1).

$$R(\rho) = \frac{A}{2\pi\mu_s'}\left(\frac{\mu_{\it eff}}{\rho^2+z_o^2}+\frac{1}{\sqrt{(\rho^2+z_o^2)^3}}\right)e^{-\mu_{\it eff}\sqrt{\rho^2+z_o^2}} \quad (1)$$

$$Z_o = \frac{1}{\mu_s'}, \mu_{\it eff} = \sqrt{3\mu_a(\mu_a+\mu_s')}$$

Here, $\mu_s'$ is the reduced scattering coefficient of the scattering substance, $\mu_a$ is an absorption coefficient, ρ is the distance between a light entering point and a detecting point (a point on the light receiving unit 7), and A is the area of the light receiving unit 7. The surface of the light receiving unit 7 is divided into meshes, and each light intensity distribution of the diffusively reflected light from one LED of the circular discrete light source unit 26 at each mesh of the light receiving unit 7 is calculated. The size of each mesh is 0.081 mm/pixel, for example. The sum of the intensity distribution of the diffusively reflected light from the plurality of LEDs is calculated. The light intensity that is detected by the light receiving unit 7 at each mesh is calculated by multiplying the light transmittance of the nonuniform filter 20 by the sum of the intensity distribution of the diffusively reflected light at each mesh.

Figure 7:
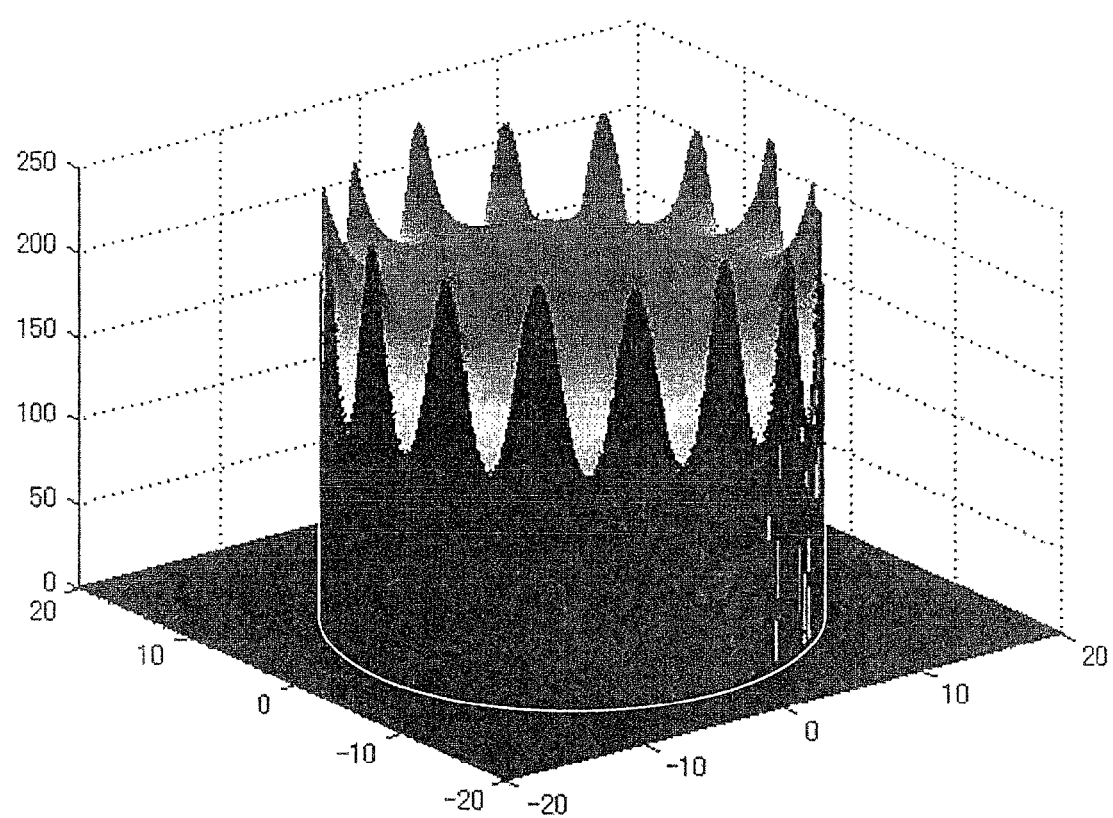
FIG. 7 is a diagram illustrating a distribution of a light intensity that is detected by the light receiving unit when a light source unit of the biometric authentication apparatus of FIG. 1 includes 16 LEDs.

FIG. 7 is a diagram illustrating the distribution of the light intensity that is detected by the light receiving unit when the circular discrete light source unit 26 includes 16 LEDs.

As illustrated in FIG. 7, the light intensity detected by the light receiving unit 7 is the largest near the area where each LED of the circular discrete light source unit 26 is disposed. The light intensity detected by the light receiving unit 7 is smaller at the center of the circle of the light receiving unit 7 or near the middle of adjacent two LEDs. The difference of the light intensities that are detected by light receiving unit 7 is reduced by the nonuniform filter 20.

Figure 8:
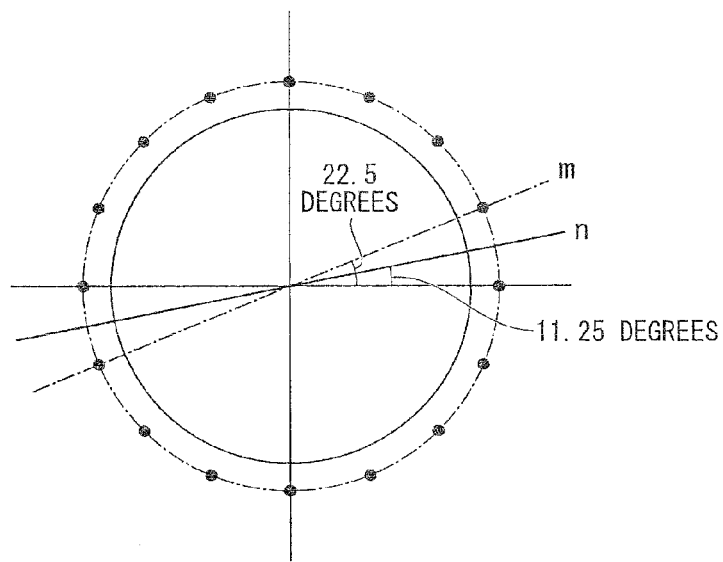
FIG. 8 is a diagram illustrating a method to measure the distribution of the light intensity of FIG. 7.

FIG. 8 is a diagram illustrating a method to measure the distribution of the light intensity.

As illustrated in FIG. 8, the light intensity of each point of the light receiving unit 7 on a line m and the light intensity of each point of the light receiving unit 7 on a line n are compared. The line m passes through the center of the light receiving unit 7 and two LEDs that face each other. The line n passes through the center of the light receiving unit 7 and a mid point of two adjacent LEDs of the circular discrete light source unit 26. As illustrated in FIG. 8, if the number of the LEDs is 16, then the line n is inclined at an angle of 11.25 degrees from a horizontal line that passes through the center of the circle. The line m is inclined at an angle of 22.5 degrees from a horizontal line that passes through the center of the circle.

The distribution of the light intensity along the line m and the distribution of the light intensity along the line n are compared, and it is determined whether or not the difference of the light intensities is less than a threshold value. If the difference of the light intensities is less than the threshold value, then the number of the LEDs is determined to be an optimal number. The difference of the light intensities has a different value based on an area of the light receiving unit 7, the number of the LEDs included in the circular discrete light source unit 26, the reduced scattering coefficient of the living body, and an absorption coefficient of the body.

By the above described method, the number of the LEDs is determined so that the difference of the light intensities between a first area of the light receiving unit 7 and a second area of the light receiving unit 7 is less than a threshold value, where the light intensity in the first area is smallest in the light receiving unit 7, and the light intensity in the second area being largest in the light receiving unit 7. In this way, the light receiving unit 7 with the optimal number of LEDs can be included in the biological information acquiring apparatus.

In the above description, the case when the circular base unit 10 of the biometric authentication apparatus 1 is in a circular form and the light receiving unit 7 is in a circular form was described. But the circular base unit 10 may be in a rectangular form and the light receiving unit 7 may be in a rectangular form. In this case, the number of the LEDs can be determined in the same way.

In the above description, as illustrated in FIG. 2, the biometric authentication apparatus 1 was worn around the wrist by rolling the band part 12a and the band part 12b around the wrist and locking the locking part 15 to the end of the band part 12a. But the biometric authentication apparatus 1 may be embedded in a mobile device. For example, the biometric authentication apparatus 1 of FIG. 1 except the band parts 12a and 12b may be included in a mobile terminal such as a mobile phone and a PDA. In this case, the authentication is performed by putting the mobile terminal including the biometric authentication apparatus 1 on a specified position of the living body.

Figure 9:
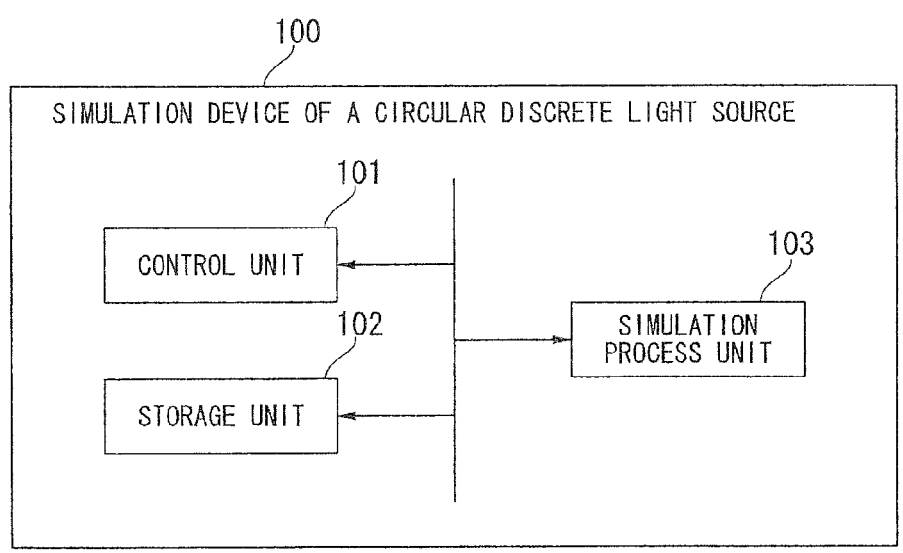
FIG. 9 is a block diagram illustrating functions of a simulation device of a circular discrete light source in accordance with the invention.

FIG. 9 is a block diagram illustrating functions of a simulation device of the circular discrete light source in accordance with the invention.

As illustrated in FIG. 9, the simulation device of the circular discrete light source 100 includes a control unit 101, a storage unit 102, and a simulation process unit 103. The simulation device of the circular discrete light source 100 may perform a simulation process that determines the optimal number of the LEDs included in the circular discrete light source unit 26, as is described above.

In this case, the simulation process unit 103 receives inputs of the number of the LEDs, the area of the light receiving unit, a coordinate of each LED when the center of the circle (or rectangle) is defined as an origin, the reduced scattering coefficient μs' of the living body (scattering substance), and the absorption coefficient μa of the body (scattering substance). The received light intensity of each point on the light receiving unit 7 is calculated using the above equation (1). The simulation process unit 103 calculates the straight-line distance between the point on the light receiving unit 7 and the coordinate of the LED. The calculated straight-line distance is determined as a distance ρ between an optical incidence point and a detecting point (a point on the light receiving unit 7).

The simulation process unit 103 determines whether or not the difference of the light intensities is less than the threshold value, by the distribution of the light intensity along the line n, which is inclined at the angle of 11.25 degrees from the horizontal line, and the distribution of the light intensity along the line m, which is inclined at the angle of 22.5 degrees from the horizontal line, based on the light intensity that is calculated at each point on the light receiving unit 7. If the difference of the light intensities is less than the threshold value, then the number of the LEDs is decreased and the difference of the light intensities is calculated again. If the difference of the light intensities becomes more than the threshold value by decreasing the number of the LEDs, then the current number of the LEDs plus one is determined as the optimal number of the LEDs. If the difference of the light intensities is more than the threshold value, then the number of the LEDs is increased and the difference of the light intensities is calculated again. If the difference of the light intensities becomes less than the threshold value by increasing the number of the LEDs, then the number of the LEDs that becomes less than the threshold value at first is determined as the optimal number of the LEDs.

The simulation device of a circular discrete light source 100 described above includes a system of a computer inside. The processes described above are stored in a storage medium, which can be read and written by the computer, in a format of a program. The processes described above are performed by reading and executing the program by the computer. The storage medium, which can be read and written by the computer, is such as a magnetic disk, a magnetic optical disc, a CD-ROM, a DVD-ROM and a semiconductor memory. The program may be delivered to the computer through a communication line and executed by the computer that receives the program.

The program described above may realize part of the functions described above. The program described above may be a difference file (difference program) that realizes the functions combined with the program that has been stored in the computer beforehand.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A biological information acquiring apparatus that acquires biological information of a living body by irradiating a light onto the body, the biological information acquiring apparatus comprising:
   light source units configured to irradiate light onto the body;
   a light receiving unit including a light receiving element, the light receiving element including pixels, each of the pixels receiving at least one of a transmission light and a reflection light by irradiating the light from the light source units onto the body, the transmission light transmitting through the body, the reflection light reflected from the body; and
   a nonuniform filter disposed on the light receiving unit and on a light path of at least one of the transmission light and the reflection light, the nonuniform filter having a light transmittance that varies with area of the nonuniform filter, and
   wherein
      the light source units are disposed around the light receiving unit discretely and the light transmittance of the nonuniform filter is set so that a light intensity of at least one of the transmission light and the reflection light is uniform over an entire surface of the light receiving element,
      each of the light source units includes LEDs, and
      the number of the light source units is determined based on a difference of the light intensity between a first area of the light receiving unit and a second area of the light receiving unit in comparison with a threshold value of the difference of the light intensity, the light intensity in the first area is smallest in the light receiving unit, the light intensity in the second area is largest in the light receiving unit, and the light intensity is calculated based on a temporarily defined number of light source units, an area of the light receiving unit, coordinates of the LED when a center of the light receiving unit is defined as an origin, a reduced scattering coefficient of the living body, an absorption coefficient of the body, and a formula for computation of a light intensity distribution of a diffusively reflected light.

2. The biological information acquiring apparatus according to claim 1, wherein
   the nonuniform filter includes a first portion disposed at or near the center of the nonuniform filter and a second portion disposed adjacent to the light source,
   wherein the light transmittance of the first portion is higher than the light transmittance of the second portion.

3. The biological information acquiring apparatus according to claim 1, wherein the biological information acquiring apparatus is attachable to a body.

4. A biological information acquiring method that acquires biological information of a living body by irradiating a light onto the body, the biological information acquiring method comprising:
   irradiating the light that is irradiated from each of light source units onto the body, the light source units being disposed around a light receiving unit discretely; and
   receiving at least one of transmission light transmitting through the living body and reflection light reflected from the body by irradiating the light from the light source units onto the body, the receiving being performed by a light receiving element including pixels through a nonuniform filter that is disposed on a light path of at least one of the transmission light and the reflection light, the nonuniform filter having a light transmittance that varies with area of the nonuniform filter, and
   wherein
      the light transmittance of the nonuniform filter is set so that a light intensity of at least one of the transmission light and the reflection light is uniform over an entire surface of the light receiving element, and
      the number of the light source units is determined based on a difference of the light intensity between a first area of the light receiving unit and a second area of the light receiving unit in comparison with a threshold value of the difference of the light intensity, the light intensity in the first area is smallest in the light receiving unit, the light intensity in the second area is largest in the light receiving unit, and the light intensity is calculated based on a temporarily defined number of light source units, an area of the light receiving unit, coordinates of each LED included in the light source units when a center of the light receiving unit is defined as an origin, a reduced scattering coefficient of the living body, an absorption coefficient of the body, and a formula for computation of a light intensity distribution of a diffusely reflected light.

5. A biometric authentication apparatus comprising:
   a biological information acquiring apparatus configured to acquire biological information of a living body by irradiating a light onto the body; and
   an authentication unit configured to perform an authentication of a person based on the biological information of the body acquired by the biological information acquiring apparatus, and wherein the biological information acquiring apparatus comprises:
  light source units configured to irradiate the light onto the living body;
  a light receiving unit including a light receiving element, the light receiving element including pixels, each of the pixels receiving at least one of a transmission light and a reflection light by irradiating the light from the light source units onto the body, the transmission light transmitting through the body, the reflection light reflected from the body; and
  a nonuniform filter disposed on the light receiving unit and on a light path of at least one of the transmission light and the reflection light, the nonuniform filter having a light transmittance that varies with area of the nonuniform filter, and
wherein the authentication unit comprises:
  a biological information storing unit configured to store the biological information of the living body acquired by the biological information acquiring apparatus as first information; and
  an authentication control unit configured to compare the first information and second information, the second information being the biological information of the living body acquired by the biological information acquiring apparatus when the authentication is performed, the authentication control unit determining completion of the authentication and outputting an enable signal if the first information coincides with the second information, and wherein
  the light source units are disposed around the light receiving unit discretely, and the light transmittance of the nonuniform filter is set so that a light intensity of at least one of the transmission light and the reflection light is uniform over an entire surface of the light receiving element,
  each of the light source units includes LEDs, and
  the number of the light source units is determined based on a difference of the light intensity between a first area of the light receiving unit and a second area of the light receiving unit in comparison with a threshold value of the difference of the light intensity, the light intensity in the first area is smallest in the light receiving unit, the light intensity in the second area is largest in the light receiving unit, and the light intensity is calculated based on a temporarily defined number of light source units, an area of the light receiving unit, coordinates of the LED when a center of the light receiving unit is defined as an origin, a reduced scattering coefficient of the living body, an absorption coefficient of the body, and a formula for computation of a light intensity distribution of a diffusively reflected light.

6. The biometric authentication apparatus according to claim 5, wherein the biometric authentication apparatus is attachable to a body.

* * * * *